Figure 1:
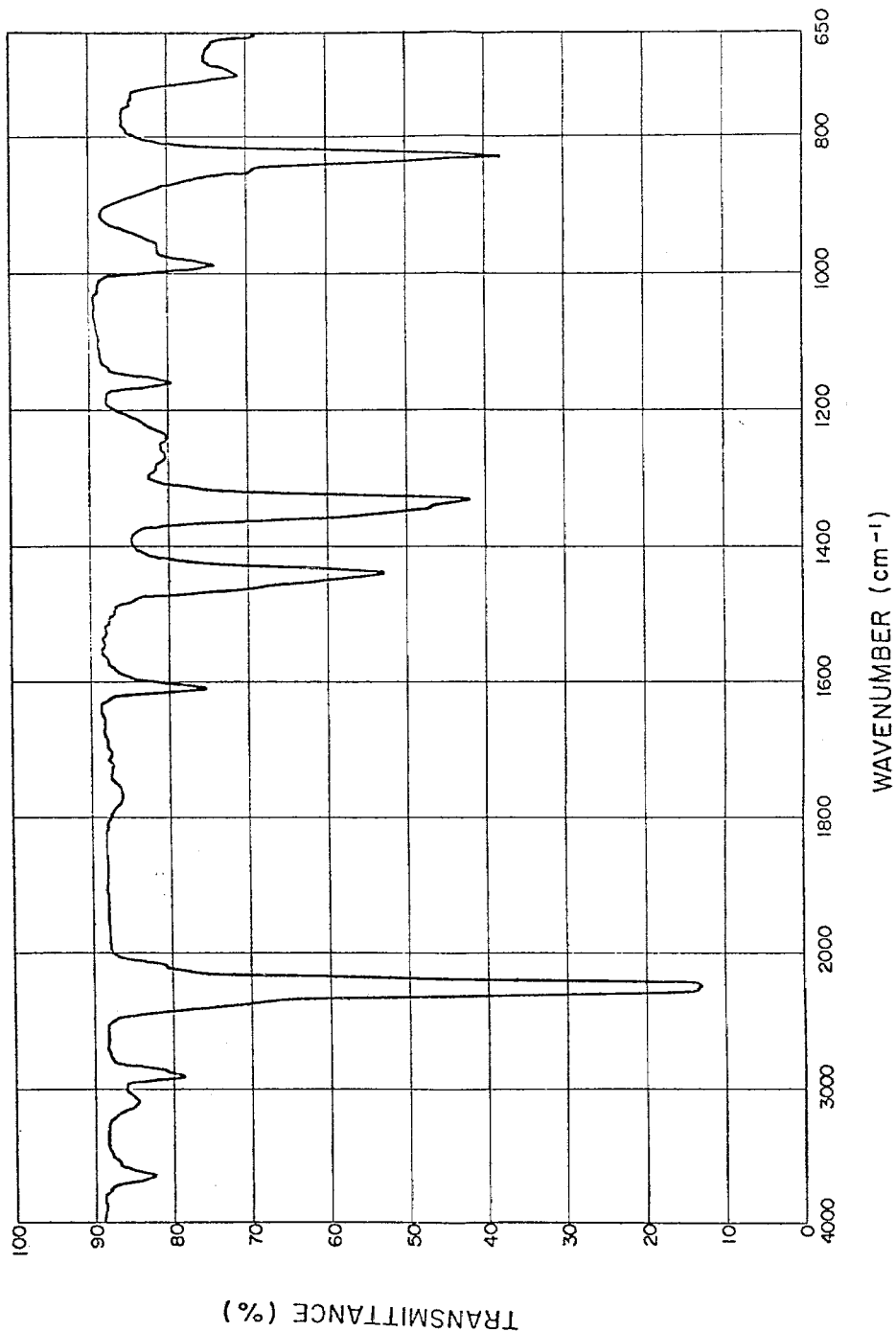

United States Patent [19]

Fujinami et al.

[11] 4,338,256
[45] Jul. 6, 1982

[54] TRIISOCYANATES

[75] Inventors: Kimiya Fujinami, Takarazuka; Ichiro Minato, Kobe; Koichi Shibata, Kawanishi, all of Japan

[73] Assignee: Takeda Chemical Industries, Ltd., Osaka, Japan

[21] Appl. No.: 154,135

[22] Filed: May 29, 1980

[30] Foreign Application Priority Data

May 29, 1979 [JP] Japan .................... 54-67171

[51] Int. Cl.³ .......................... C07C 119/045
[52] U.S. Cl. ................. 260/453 A; 260/453 AR; 260/453 PH; 528/44
[58] Field of Search ...... 260/453 A, 453 AR, 453 PH

[56] References Cited

U.S. PATENT DOCUMENTS 3,551,469 12/1970 Weyland et al. .............. 260/453 A
4,059,610 11/1977 Handa et al. ................. 260/453 P X
4,113,705 9/1978 Bock et al. ................... 260/453 A X Primary Examiner—Dolph H. Torrence
Attorney, Agent, or Firm—Wenderoth, Lind & Ponack

[57] ABSTRACT

The present invention provides novel triisocyanate compounds of the formula:

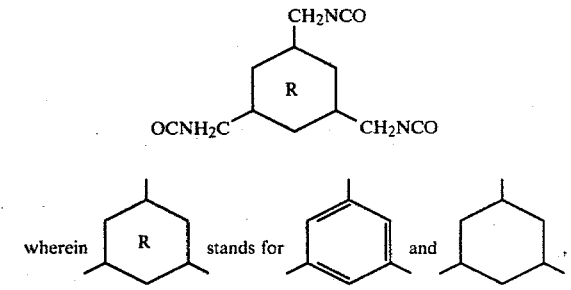

the production thereof and the use thereof for polyurethane resins, especially, for solvent-free or high solids polyurethane coatings.

1 Claim, 2 Drawing Figures

TRIISOCYANATES

The present invention relates to novel triisocyanate compounds, which can be converted to plastics, particularly polyurethane resins with improved weatherability, especially excellent polyurethane coatings of a solvent-free or high-solids type, to a process for producing the same, and to use of the same, for polyurethane resins.

Among isocyanate compounds employable as a raw material for polyurethanes, aromatic isocyanates such as tolylene diisocyanate (TDI) and diphenylmethane diisocyanate (MDI) are utilized in large quantities. Yet, polyurethanes derived from these aromatic isocyanate compounds suffer from the serious defect of their tendency to yellow with time elapsed, and such defect presents one of the restrictions on their application fields.

A great variety of attempts have so far been made to produce polyurethane compounds with improved non-yellowing properties, and in preparing polyurethane resins there have been employed, such materials as aliphatic or aromatic-aliphatic polyisocyanates, such as hexamethylene diisocyanate (HDI), xylylene diisocyanate (XDI), hydrogenated xylylene diisocyanate (H$_6$XDI), hydrogenated diphenylmethane diisocyanate (H$_{12}$MDS), isophoron diisocyanate (IPDI) and lysine diisocyanate ester (LDI). Nevertheless, these have a fewer number of functional groups per molecule and a high vapor pressure at ambient temperature, and therefore must to be converted to adducts with polyfunctional alcohols, amines, water, etc. or those among isocyanates such as dimers, trimers and carbodiimides, when these are applied as coatings, etc. Yet, these adducts, which necessitate consumption of the isocyanate groups for the addition reaction, show a decreased content of the isocyanate groups available for further reaction, with increase in viscosity, which makes it very difficult to convert them to the solvent-free or high-solids coatings recently being strongly demanded in view of the increased pollution control demands. In order to lower the content of the isocyanate monomer, which presents the hygienically serious problem in the case of such adducts at working sites, complex technologies and costly production facilities are required.

Consequently, strongly demanded are the polyisocyanates which eliminate the defects of isocyanate compounds currently employed and can afford polyurethane resins with superior weatherability, further being convertible to solvent-free or high-solids coatings.

The present inventors, after extensive and thorough research and investigation conducted for the purpose of obtaining a polyisocyanate fulfilling such requisites with the use of readily available and relatively low-priced starting materials, have come to complete the present invention.

Thus, the present invention provides:

1. A triisocyanate compound of the general formula (I):

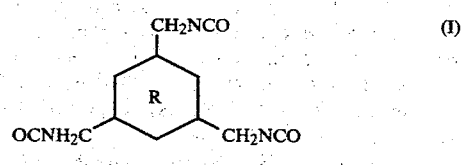

wherein

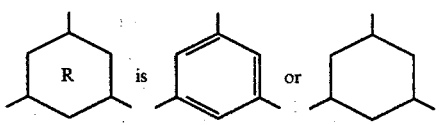

2. A process for producing a triisocyanate compound of the general formula (I):

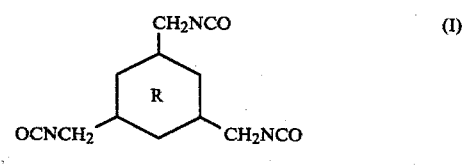

wherein

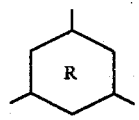

is as defined below, characterized in that said process comprises reacting a triamine compound of the general formula (II):

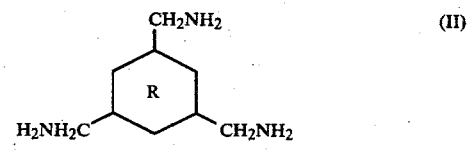

wherein

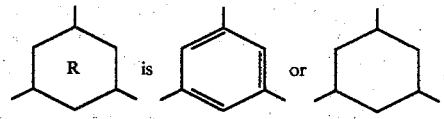

or its salt with phosgene, and

3. A process for producing a polyurethane resin, characterized in that said process comprises reacting a triisocyanate compound of the general formula (I):

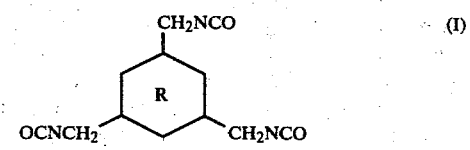

wherein

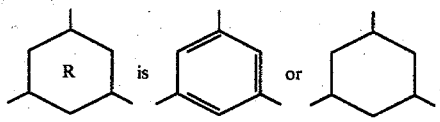

with an active hydrogen compound.

The above-mentioned triisocyanate compound of the general formula (I) are novel compounds which have not been described in the known literature.

The compound of the general formula (I) wherein

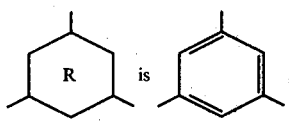

is 1,3,5-tris(isocyanatomethyl)benzene (hereinafter referred to sometimes as "MTI"), while the one wherein

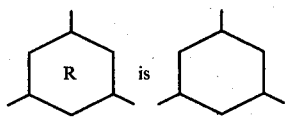

is 1,3,5-tris(isocyanatomethyl)cyclohexane (hereinafter rererred to sometimes as "H$_6$MTI"), and these can be produced by phosgenating the corresponding triamine compounds (II), or 1,3,5-tris(aminomethyl)benzene (hereinafter referred to sometimes as "MTA"0 and 1,3,5-tris(aminomethyl)cyclohexane (hereinafter referred to sometimes as "H$_6$MTA"), respectively.

Phosgenation of the triamines (II) can be carried out in accordance with the procedures conventional per se. Among these, one is the procedure termed the so-called cold.hot phosgenation, which comprises adding the starting triamine compounds or a solution of said triamine compounds in an organic solvent dropwise, under stirring, to cooled liquid phosgene or a solution of phosgene in an organic solvent, and elevating the reaction temperature with feeding of phosgene to allow the reaction to proceed and go to completion; the other is the process which comprises adding an organic solvent to a salt of the starting triamine to a slurry form or adding an acid to a solution of the triamine in an organic solvent to obtain a slurry of the triamine salt, and elevating gradually the temperature while feeding phosgene to the slurry to allow the phosgenation reaction to proceed and go to completion.

The starting triamines with a high degree of purity may be utilized, although the starting triamines containing a small amount of impurities by-produced during production of said triamines can even be used as well.

As examples of the organic solvent which is useful in the phosgenation reaction may be mentioned aromatic hydrocarbons, halogenated aromatic hydrocarbons, halogenated aliphatic hydrocarbons, halogenated alicyclic hydrocarbons, etc., and, among these, halogenated aromatic hydrocarbons such as chlorobenzene and o-dichlorobenzene are desirable. The salts of the triamines which are operable include acetic acid salts, hydrochloric acid salts, sulfuric acid salts, carbamic acid salts and the like, and preferred among others is a carbamic acid salt formed by reacting the triamine with carbon dioxide gas. Phosgene can be used either in the gaseous or liquid form, and a phosgene dimer (trichloromethyl chloroformate), which is regarded as a precursor of phosgene in this industrial field, can be used in place of phosgene.

Referring to the temperature in the reaction between the triamine compound (I) and phosgene, too much elevated temperature results in formation of a larger amount of by-products, while too much of a reduced temperature leads to a lowered reaction rate, and it is desirable to select the reaction temperature in the range of $-20°$ to $180°$ C.

Out of the reaction solution with which phosgenation is completed in this manner, excessive phosgene and reaction solvents are removed, and vacuum distillation is then effected, thus resulting in the desired triisocyanate compound (I) in a high purity.

The above-mentioned triamine compounds of the general formula (II) are also novel compounds which have not been described in the known literature, and can be produced, for example, by the procedure to be described below.

Thus, 1,3,5-tris(aminomethyl)benzene (MTA) can be obtained by hydrogenating, for example, 1,3,5-tricyanobenzene (hereinafter referred to sometimes as "MTN") in the presence of a catalyst, while H$_6$MTA can be obtained by hydrogenating MTA in the presence of a catalyst or by subjecting MTN, simultaneously in the presence of a catalyst, to the hydrogenation of the cyano group and the nuclear reduction of the benzene ring.

First, the production of MTA by hydrogenation of MTN is conducted in the liquid phase in the presence of hydrogen, whereby the use of a solvent provides good results.

As the solvent may be used aromatic hydrocarbons such as benzene, toluene and xylene; alcohols such as methanol, ethanol, propanol, isopropanol and isobutanol; ethers such as dioxane and tetrahydrofuran. Also, other solvents inert under the above reaction conditions may be employed, such as water and liquid ammonia, although the solvents based on alcohols or aromatic hydrocarbons-alcohol mixtures are preferred because they permit one to reduce the amount of catalyst, while resulting in a smaller decrease in the yield of the objective compound. The said solvents may be used alone or two or more solvents may be used in admixture. As to the amount of the solvent, this is not specifically restricted, but 0.5 to 10 times by volume, and preferably 1 to 6 times by volume relative to the starting trinitrile compound provides satisfactory results. Naturally, the use of larger quantities of solvent does not interfere greatly with the reaction but, large amounts are not economical from a commercial point of view. By adding a basic substance, for example, a hydroxide or an alcoholate of alkali metals such as lithium hydroxide, sodium hydroxide, potassium hydroxide, sodium methylate and sodium ethylate at a rate of 0.05 to 40% by weight, preferably 0.5 to 20% by weight, based on the starting trinitrile, at the same time, there may be obtained more desirable results in that the amount of catalyst necessary to effect the reaction may be decreased and the reaction time may be shortened. In conducting the hydrogenation, use is made of hydrogen, and it is advisable to conduct the reaction in a pressure vessel, such as an autoclave, in the case of using a higher reaction pressure. The reaction pressure is in the region of 30 to 300 kg/cm$^2$G, preferably, in the region of 30 to 150 kg/cm$^2$G, whereas the reaction temperature is in the range of $-10°$ to $150°$ C., preferably, in the range of $40°$ to $120°$ C. In carrying out the hydrogenation, normally, it is desirable to use a catalyst. As examples of a catalyst may be mentioned Raney cobalt, Raney nickel, Raney nickel.chromium, platinum, palladium, ruthenium and rhodium. These may be used alone or as a mixture of not less than two kinds and the combination of Raney nickel.chromium, among others, produces preferable results. By selecting a suitable solvent system and an alkali additive, there may be produced such conditions as to bring about a relatively small decrease in yield, even when a lower-priced Raney-nickel catalyst is utilized or where the amount of the catalyst is reduced.

MTA is made up of colorless crystals at ambient temperature and, upon heating at about 50° C., turns into a colorless, clear liquid. After being purified under normal conditions, MTA shows a melting point of 49° to 51° C. and a boiling point of 136° to 139° C./0.4 mmHg.

$H_6MTA$ may be obtained by hydrogenating MTA or hydrogenating MTN.

The hydrogenation of MTA is generally conducted in the liquid phase in the presence of hydrogen, with a solvent being employed, if necessary. As the solvent one or more different types may be used, for example, water, ethanol, methanol, propanol, isopropanol, isobutanol, dioxane, acetic acid, tetrahydrofuran, etc., although water is advantageous in terms of cost and an alcohol-water mixed solvent is preferred in that it allows for a reduction in the amount of catalyst, with a smaller decrease in the yield of the objective compound. The solvent, among the reaction conditions selected, is not required. Yet, when a solvent is used, 0.05 to 10 times by volume, preferably, 0.1 to 5 times by volume, of the starting MTA may provide the satisfactory results. By adding 0.5 to 20% by weight, preferably, 0.1 to 10% by weight, relative to MTA, of a basic substance, for example, a hydroxide or carbonate of an alkali metal and an alkali earth metal such as lithium hydroxide, sodium hydroxide, potassium hydroxide, calcium hydroxide, barium hydroxide and sodium carbonate, there may be obtained even more desirable results. In conducting the hydrogenation, use is made of hydrogen gas. While the reaction vessel is not specifically limited in design and construction, providing it can withstand the reaction conditions, it is nevertheless advisable to conduct the reaction in a pressure vessel, such as an autoclave, in the case of conducting the reaction at a higher reaction pressure. The reaction pressure is in the region of 5 to 300 kg/cm$^2$G, preferably, in the region of 5 to 150 kg/cm$^2$G, whereas the reaction temperature is in the range of $-10°$ to 200° C., preferably, in the range of 50° to 150° C. In carrying out the hydrogenation, normally, it is desirable to use a catalyst. As examples of the catalyst may be mentioned Raney nickel, Raney nickel.chromium, palladium, platinum, rhodium, ruthenium, etc. These catalysts are used alone or as a mixture of not less than two kinds, and, as the case may be, supported on a carrier, such as activated carbon, silica gel, alumina, diatomaceous earth and pumice, to obtain more desirable catalytic results. Among these, a ruthenium catalyst can be the most desirable one, because it allows a reduction in the addition amount of catalyst, with a smaller decrease in the yield, especially when water containing a small amount of an alkali metal hydroxide or carbonate, an alcohol or a mixture thereof is employed as a solvent.

$H_6MTA$ can also be directly obtained through hydrogenation of MTN.

In hydrogenating MTN, there may be produced more desirable results by conducting the liquid-phase reaction in the presence of hydrogen and employing a solvent. As examples of the solvent may be mentioned aromatic hydrocarbons such as benzene, toluene and xylene; alcohols such as methanol, ethanol, propanol, isopropanol and isobutanol; ethers such as dioxane and tetrahydrofuran, and others, inclusive of acetic acid, liquid ammonia and water, etc. One or a mixture of not less than two kinds of solvents can be used, although water, ethanol or their mixture, affords the desired product in a high yield, and is therefore the preferred solvent. When the reaction is conducted in the coexistence of ammonia or in a liquid ammonia solvent, the formation of by-products can be prevented, and similar effects can be achieved by adding to the solvent reaction, 0.01 to 5% of, and preferably, 0.05 to 3.0% of, a basic substance, for example, caustic soda or caustic potash. As to the amount of the solvent to be used, 0.5 to 10 times by volume of MTN preferably, 1 to 6 times by volume thereof, is the range in which satisfactory results can be produced.

In carrying out the hydrogenation, use is made of hydrogen gas and a reaction vessel is not specifically restricted, although the vessel must be able to withstand the selected reaction conditions. It is advisable, in the case of an increased reaction pressure, to conduct the reaction in such a pressure vessel as an autoclave. The reaction pressure is in the region of 5 to 300 kg/cm$^2$G, preferably, in the region of 30 to 200 kg/cm$^2$G, while the reaction temperature is in the range of $-10°$ to 250° C., preferably, in the range of 50° to 200° C.

It is desirable to use a catalyst in the hydrogenation. As examples of a catalyst, there may be mentioned Raney cobalt, Raney nickel, Raney nickel.chromium, palladium, platinum, rhodium, ruthenium, etc. Such catalyst may be used alone or as a mixture of not less than two kinds, and, among others, the rhodium catalyst is preferred because it produces $H_6MTA$ in an increased yield. When water, ethanol or a mixture thereof is used as a solvent, this results in a higher yield of the objective compound of the hydrogenation reaction, and this may be considered as the most important reaction condition in the case of a one-step production of $H_6MTA$ from MTN.

$H_6MTA$ is a colorless clear liquid at ambient temperature and, upon cooling to 0° C., neither solidifies nor produces a precipitate.

The triisocyanate compounds, according to the present invention, possess various advantages over conventionally known polyisocyanates. That is to say, they are completely odorless, are non-irritants, and are by far less viscous than the prior art polyisocyanates. They are also colorless and clear liquids at room temperature, and thus are of great utility, particularly as a component for solvent-free or high-solid urethane coatings. Further, because of the low cost of these starting materials and the simplicity of the production process employed, the materials have very high industrial value.

The triisocyanate compounds, according to the present invention, can afford various polyurethanes through a variety of polyaddition process, utilizing the reaction between isocyanates and active hydrogen compounds, well known in the industry. The triisocyanates of the present invention, besides being utilizable directly in the original form, can be further used as a variety of modified products known in the related industry (as the dimer, trimer, carbodiimide, etc.) and also in the form of polymers, which comprises reacting them with polyols, polyamines, aminoalcohols, water, etc. In the case of such application fields as baking paints, furthermore, they can be used in the form of blocked isocyanates with the use of a variety of known blocking agents.

As examples of a suitable masking agent, there may be mentioned phenols such as phenol, cresol and isononylphenol; oximes such as butanone oxime and benzophenone oxime; lactams such as caprolactam, etc., alcohols such as methanol; esters such as acetoacetate and malonate; triazoles such as benzotriazole, mercaptane, and others.

Examples of the active hydrogen compound, which is suitable for the reaction with the triisocyanates of the present invention or their corresponding, masked polyisocyanates, include compounds containing at least two of the hydrogen atoms reactable with the isocyanate and having a molecular weight of 400 to 10,000, in general. Among these compounds, particularly suitable for hydroxyl compounds, and compounds having 2 to 8 hydroxyl groups, especially with a molecular weight of 800 to 10,000; more preferably, 1000 to 6000, are preferred. Also, there may be used such materials as polyesters, polyethers, polythioethers, polyacetals, polycarbonates, polyester amides, or compounds similar thereto, having hydroxyl groups of at least 2, generally, 2 to 8, and preferably, 2 to 4. These compounds are known per se as the raw materials for polyurethanes.

As examples of the suitable hydroxyl containing polyesters, may be mentioned the reaction products from polyfunctional, preferably divalent, alcohols (trifunctional alcohol may be added to this) and polybasic materials, preferably dibasic, carboxylic acid. Examples of such acids, include succinic acid, adipic acid, azelaic acid, sebacic acid, phthalic acid, isophthalic acid, trimellitic acid, phthalic anhydride, tetrahydrophthalic anhydride, hexahydrophthalic anhydride, maleic acid, maleic anhydride, fumaric acid, and the like. Examples of suitable polyalcohols include ethylene glycol, propylene glycol-(1,2) and -(1,3), butylene glycol-(1,4) and -(2,3), hexanediol(1,6), neopentyl glycol, cyclohexanedimethanol (1,4-bis-hydroxymethylcyclohexane), glycerol, trimethylol propane, pentaerythritol, diethylene glycol, triethylene glycol, tetraethylene glycol, pentaethylene glycol, polyethylene glycol, dipropylene glycol, polypropylene glycol, butylene glycol, polybutylene glycol, etc. In addition to the above-mentioned polyhydroxy polyesters, polyhydroxy polyethers known in the field of the polyurethane chemistry can also be used for these novel triisocyanates. As examples of such polyhydroxy polyethers may be mentioned per se known polyethers having the hydroxyl groups of at least 2, generally, 2 to 8, and preferably 2 to 3 hydroxyl groups. Such polyethers can be produced by polymerizing in the presence of, for example, boron trifluoride, epoxides themselves, such as ethylene oxide, propylene oxide, butylene oxide, tetrahydrofuran, styrene oxide and epichlorohydrin, or by allowing these epoxides, either as a mixture or successively in turn, to add on to the polyethers, starting components containing reactive hydrogen atoms. As examples of such starting compounds containing reactive hydrogen may be mentioned water, alcohols, amines, etc., such as ethylene glycol, propylene glycol-(1,3) or -(1,2), trimethylol propane, 4,4'-dihydroxydiphenylpropane aniline, ammonia, ethanolamine and ethylene diamine.

Specific examples of the above compounds are described, for example, in the following publication: "High Polymers; Vol. XVI, Polyurethanes, Chemistry and Technology", edited by Saunders and Frisch, Interscience Publishers, New York/London, vol. 1, 1962, pages 32 through 42, pages 44 through 54; vol. 2, 1964, pages 5 through 6 and pages 198 through 199.

Hydroxy-group containing vinylic polymers can also be used as a reactant for the triisocyanates of the present invention. Such vinylic polymers are known reaction products, consisting of copolymers from ethylenically unsaturated monomers of containing hydroxyl groups and other kinds of ethylenically unsaturated compounds such as ethylenically unsaturated esters and hydrocarbons. Examples of such products include copolymers containing the following hydroxyl monomer components: monohydroxy- and polyhydroxyalkyl maleate and fumarate, eg., hydroxyethyl fumarate and compounds similar thereto; acrylates and methacrylates having hydroxyl groups e.g., trimethylolpropane monomethacrylate, 2-hydroxyethyl acrylate and 2-hydroxyethyl methacrylate, 2(or 3)-hydroxypropyl acrylate and methacrylate, 4-hydroxybutyl acrylate and methacrylate, etc., and hydroxyvinyl compounds, e.g., hydroxyethyl vinyl ether and allyl alcohol. Furthermore, partially hydrolyzed products of homopolymers of vinyl acetate, etc., or copolymers thereof with ethylenically unsaturated compounds can also be used as such polyols.

Acid-group containing polymers obtained by copolymerizing unsaturated acids such as maleic acid, acrylic acid and methacrylic acid can be used in the above-mentioned lacquers, as well.

The novel triisocyanates, according to the present invention or the masked triisocyanates corresponding to them, in case where they are utilized for the above-mentioned two can type polyurethane lacquers, can be mixed not only with relatively high-molecular weight polyhydroxy compounds as described above, but also any low-molecular weight polyhydroxy compounds having a molecular weight in the range of 62 to 400. In many instances, it is advantageous to use a mixture of the above-mentioned relatively high-molecular weight polyhydroxy compounds and the aforementioned type of low-molecular weight polyhydroxy compounds. The NCO/OH ratio in such two can type polyurethane lacquers is normally 0.8:1 to 1.2:1.

As examples of suitable low-molecular weight polyhydroxy compounds having the above-mentioned molecular weight range, there may be mentioned diols and/or triols having hydroxyl groups bonded by the linkage of an aliphatic or alicyclic type, such as ethylene glycol, propane-1,2-diol, propane-1,3-diol, hexamethylene glycol, trimethylolpropane, glycerol, trihydroxyhexane, 1,2-dihydroxycyclohexane, and 1,4-dihydroxycyclohexane. Also suitable are low-molecular weight polyols having ether groups, such as diethylene glycol, triethylene glycol, tetraethylene glycol, dipropylene glycol, tripropylene glycol and tetrapropylene glycol.

In principle, a mixture of the aforementioned polyhydroxy compounds may be utilized, provided, however, that the components in the mixture must be compatible with one another.

A lacquer produced in accordance with the present invention and using the novel triisocyanates or the masked triisocyanates corresponding to them offer the following great advantages: that is to say, such lacquer can be used in the absence of a solvent, and produce weathering-resistant coating films (coated films) with excellent mechanical properties without evolution of air bubbles.

During the production of such lacquer compositions, the addition of a moisture absorbing agent or a dehydrating agent is not necessary.

The lacquer of the present invention can be mixed with pigments and fillers in an apparatus ordinarily employed by the lacquer industry.

Needless to say, other raw materials and/or auxiliary materials for a lacquer, such as a cellulose ester, a levelling agent, a plasticizer, a silicon oil, resins and/or other materials conventionally employed can be added.

In order to control the reactivity of such polyurethane lacquer, known catalysts may be used. The lacquer can be applied for covering the surface of a substrate by the conventional procedures, for example, by brushing, spraying and dipping. The lacquer is especially valuable for covering of arbitrary articles produced from wood, metal, plastics, or other materials. The triisocyanate compounds according to the present invention can be utilized as raw materials for polyurethane adhesives, foams, artificial leather, filling agents, etc. in addition to urethane coatings.

REFERENCE EXAMPLE 1

In an autoclave of a 300-ml content fitted with an electromagnetic agitator was placed for tight sealing a mixture of 15 g of 1,3,5-tricyanobenzene (MTN), 15 g of Raney-nickel.chromium catalyst prepared according to the conventional method (atomic ratio of Ni:Cr=49:1), 27 ml of methanol, 63 ml of m-xylene and 0.18 g of caustic soda, and hydrogen was charged at an initial pressure of 100 kg/cm$^2$G to conduct the reaction at 100° C., resulting in the absorption of 0.59 mole of hydrogen over a 35-minute period. The catalyst was filtrated out and the solvent was distilled off, followed by conducting vacuum distillation, thus resulting in 12.8 g of 1,3,5-tris(aminomethyl)benzene (MTA).

The MTA composed of was colorless crystals at ambient temperature, had a melting point of 49° to 51° C. and a boiling point of 136° to 139° C./0.4 mmHg, and, upon heating at about 50° C., turns into a colorless, clear liquid.

REFERENCE EXAMPLE 2

In an autoclave of a 300-ml content fitted with an electromagnetic agitator was placed for tight sealing 30 g of 1,3,5-tris(aminomethyl)benzene (MTA), together with 3 g of a 5% ruthenium-alumina catalyst (produced by Japan Engelhardt Co.), 60 g of water and 0.75 o of caustic soda, and high-pressure hydrogen was charged at 120 kg/cm$^2$G in an initial pressure to react at 115° C. for 25 minutes, resulting in the absorption of 0.61 mole of hydrogen.

The catalyst was filtered out, and the solvent was distilled off, followed by vacuum distillation, resulting in 26.8 g of 1,3,5-tris(aminomethyl)cyclohexane (H$_6$MTA). The H$_6$MTA was colorless, clear, less viscous liquid having a boiling point of 127° to 128° C./1 mmHg.

REFERENCE EXAMPLE 3

In an autoclave of a 300-ml content fitted with an electromagnetic agitator was placed for tight sealing 20 g of 1,3,5-tricyanobenzene (MTN) together with 80 ml of 25% aqueous ammonia, 300 mg of caustic soda and 4 g of a 5% rhodium-alumina catalyst being commercially available, and the mixture was subjected to reaction under high-pressure hydrogen of 120 kg/cm$^2$G in initial pressure at 105° C. for 70 minutes, resulting in the absorption of 0.95 mole of hydrogen. By the above procedure was obtained, in a yield of 45%, H$_6$MTA having both the nitrile and benzene ring reduced.

EXAMPLE 1

In 1200 ml of o-dichlorobenzene in a 2-l four-necked flask was dissolved, under warming conditions 90.0 g of 1,3,5-tris(aminomethyl)benzene (MTA). Carbon dioxide gas was introduced in the resultant amine solution until no weight increase was observed, resulting in a slurry of colorless crystals. The slurry-formed material was maintained at a temperature of not higher than 10° for 30 minutes, while blowing a phosgene gas under stirring, and the temperature was elevated to 130° C. over a 2 hour period under feeding of phosgene, followed by maintaining at 130° C. for 5 hours. As the phosgenation reaction proceeds, the slurry turned to a solution and, eventually, to a uniform, slightly yellowish, clear solution.

After the completion of the phosgenation reaction, phosgene was released from the solution by blowing nitrogen gas, and the solvent of o-dichlorobenzene was distilled off under reduced pressure. Vacuum distillation of the resultant crude isocyanate afforded 112.9 g of 1,3,5-tris(isocyanatomethyl)benzene (MTI) of a boiling point of 173° to 175° C./0.4 mmHg (the molar yield of 85.2%). The MTI was a less viscous liquid, even at 5° C., and completely free from odor peculiar to isocyanates. It was found to have an amine equivalent of 83.25 (the theoretical value of 81.1). The IR spectra of MTI, thus obtained, was shown in FIG. 1.

The resultant MTI contained trace amounts of impurities, and in order to make a definite identification thereof, the following experiment was carried out: a small amount of MTI was reacted with a large quantity of methanol to obtain its methylurethane derivative, and recrystallization of the same from acetone as the solvent afforded trimethylurethane of MTI as white crystals (recrystallization yield of 71.5%); and the results of elementary analysis on the purified trimethylurethane compound was found to be in good agreement with the theoretical value. Melting point; 155°–156° C. Elementary analysis (for $C_{15}H_{21}N_3O_6$):

|   | Calcd. (%) | Found (%) |
|---|---|---|
| C | 53.09 | 53.03 |
| H | 6.24 | 6.01 |
| N | 12.38 | 12.09 |

EXAMPLE 2

Figure 2:
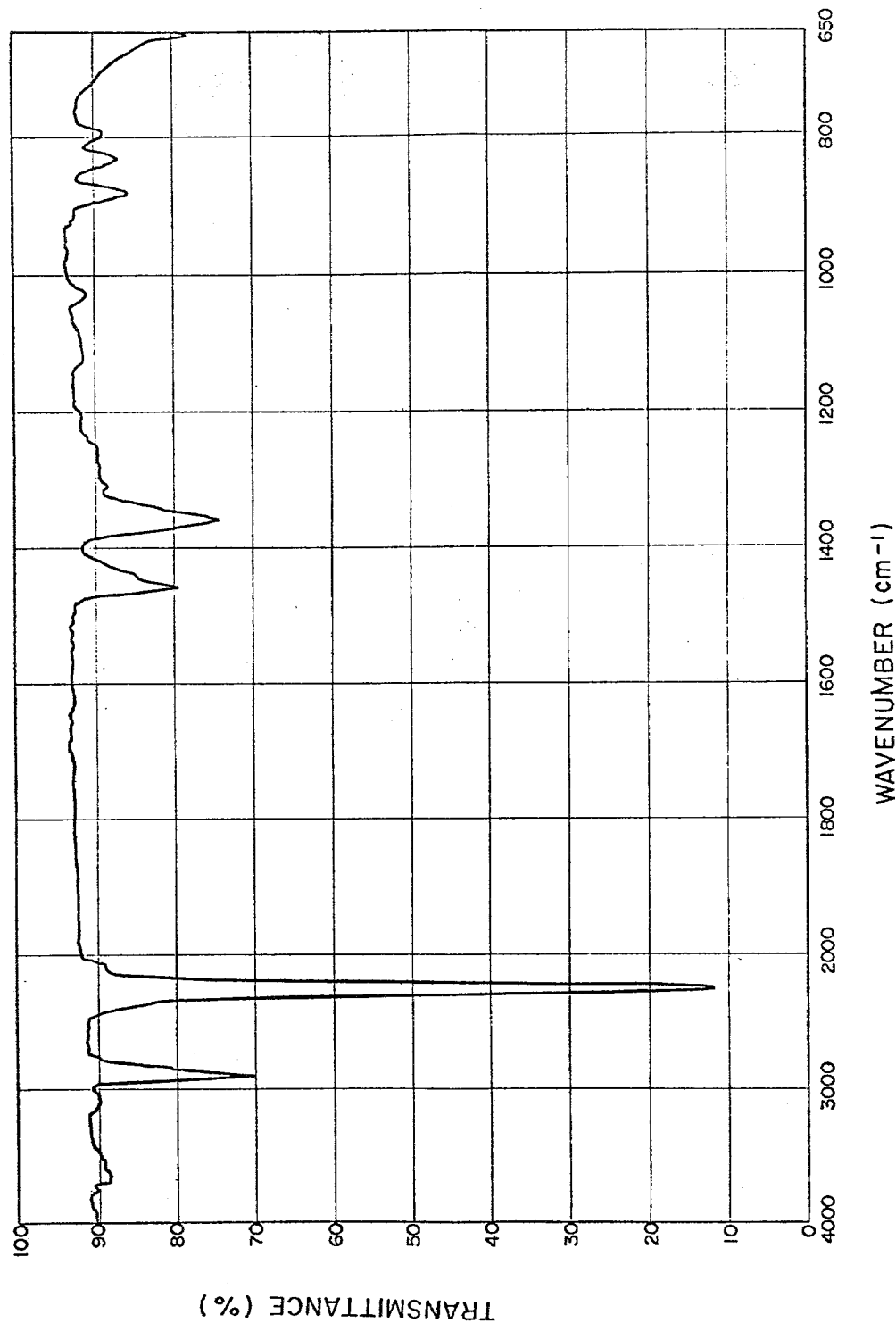

Phosgenation was carried out in the same manner as in Example 1, except that 70.0 g of 1,3,5-tris-(aminomethyl)-cyclohexane (H$_6$MTA) was used in place of 1,3,5-tris(aminomethyl)benzene (MTA) and that the reaction temperature was elevated from 10° C. to 120° C. over a 6-hour period, followed by maintaining the temperature at 120° C. for 6 hours. By the above procedure, there was obtained 91.8 g of 1,3,5-tris(isocyanatomethyl)cyclohexane (HD$_6$MTI) of a boiling point of 170° to 174° C./0.53 mmHg (molar yield of 90.1%). The H$_6$MTI was a liquid which is less viscous, even at 5° C., and free from odor. The found amine equivalent was 84.71 (the calculated one of 83.08). The IR spectra of H$_6$MTI thus obtained was shown in FIG. 2.

A trimethylurethane derivative of H$_6$MTI, purified through methylurethane formation and recrystallization from acetone as was the case with MTI, had the following values of elementary analysis: Elementary analysis (for $C_{15}H_{27}N_3O_6$);

|   | Calcd. (%) | Found (%) |
|---|---|---|
| C | 52.16 | 52.27 |
| H | 7.88 | 8.00 |
| N | 12.17 | 11.88 |

EXAMPLE 3

In a 1-l, four-necked flask was charged 250 g of o-dichlorobenzene, which was then allowed to absorb phosgene under ice-cooling. While phosgene was blown into it, a solution of 45.2 g of 1,3,5-tris(aminomethyl)benzene (MTA) in 500 g of o-dichlorobenzene was added dropwise over a 100-minute period. As the addition proceeds, the liquid contained in the flask showed a rising viscosity and turned into slurry form. After the addition of the amine was completed, the reaction mixture was maintained at a temperature not higher than 10° C. for 30 minutes and heated up to 130° C. over a 5-hour period, while phosgene was blown in, followed by reacting at 130° C. for 6 hours to thus complete the phosgenation.

By the same procedure as in Example 1, there was obtained a 54.8 g (yield of 82.4%) of MTI.

EXAMPLE 4

In the same manner as in Example 3, 42.3 g of 1,3,5-tris(aminomethyl)cyclohexane ($H_6MTA$) was phosgenated to give 53.0 g (yield of 86.1%) of $H_6MTI$.

EXAMPLE 5

Using the MTI as obtained in Example 1, a highly non-volatile two-can type urethane coating was prepared.

| Component A: | |
|---|---|
| (1) Acrylic polyol [a compolymer solution with 65% of nonvolatile content and 65 of OH value produced by copolymerizing in a toluene/butyl acetate mixed solvent (1:1) 50% of styrene, 23.2% of 2-hydroxyethyl methacrylate and 26.8% of n-butyl acrylate] | 863 parts |
| (2) Titanium dioxide powder | 429.5 parts |
| (3) Ethyl acetate/butyl acetate/cellosolve acetate (1/1/1) | 276.1 parts |
| Component B: | |
| MTI | 83.3 parts |

The component A, with the pigment well dispersed by means of a ball mill, was mixed with the component B in such a proportion as may realize a NCO/OH=1/1. The mixture showed 65% of a non-volatile content and 24 seconds of viscosity, as determined by the use of Ford cup #4 at 25° C. It was immediately spray-applied on a soft steel plate, surface-treated with phosphoric acid to produce a dried coating film of a thickness of 30 to 40μ. After conducting conditioning at 25° C. for 7 days, determination of the physical properties and weathering test were effected with the coating film.

| Coating film thickness: | 30 to 40μ |
|---|---|
| Pencile hardness | H |
| Erichsen extrusion test | 8.5 mm |
| Cross cut test | 100/100 |
| Sunshine type Weather-O-Meter | 500 hr ΔE 1.2 |

EXAMPLES 6-8

Using MTI as obtained in Example 1 or $H_6MTI$ as obtained in Example 2 in combination with a variety of polyols, a two-can type urethane coating with a high non-volatile content was prepared in the same manner as stated in Example 5 to investigate the physical properties and weatherabilities of the resultant coating films. The results obtained were tabulated in Table 1.

TABLE 1

| Experiment No. | 6 | 7 | 8 |
|---|---|---|---|
| Component A: | | | |
| Polyol (parts) | Polyester polyol (I), 255 | Acrylic polyol, 863 | Polyester polyol (II), 243.9 |
| Titanium dioxide (parts) | 225.5 | 430.4 | 219.1 |
| Solvent (parts) | BA, 241.6 | EA/BA/CA (1/1/1)277.4 | BA 136.9 |
| Component B: (parts) | MTI, 83.3 | $H_6MTI$, 84.7 | $H_6MTI$, 84.7 |
| At the time of mixing of Components, A and B: | | | |
| Non-volatile content (%) | 70 | 65 | 80 |
| Viscosity (sec.) | 24 | 26 | 27 |
| Physical properties: | | | |
| Thickness of coating film (μ) | 30 to 40 | 30 to 40 | 30 to 40 |
| Pencile hardness | HB | H | HB |
| Erichsen (mm) | 8.5 | 8.2 | 8.0 |
| Cross cut test | 100/100 | 100/100 | 100/100 |
| Weatherability, ΔE | 1.6 | 0.3 | 0.7 |

Remarks:

Polyester polyol (I); A condensate, with 100% of a non-volatile content and an OH value of 22 was produced from 2 moles of adipic acid, 1 mole of dipropylene glycol, 2 moles of trimethylol propane and 1 mole of coconut-oil based fatty acid.

Acrylic polyol; A copolymer solution with 65% of non-volatile content and an OH value of 65 was produced by copolymerizing 50% of styrene, 23.2% of 2-hydroxyethyl methacrylate and 26.8% of n-butyl acrylate in toluene-butyl acetate (1:1).

Polyester polyol II; A condensate, with 100% of non-volatile content and an OH value of 230, was produced from 2 moles of adipic acid, 1 mole of diethylene glycol, 2 moles of trimethylol propane and 1 mole of coconut-oil based fatty acid.

BA: Butyl acetate
EA: Ethyl acetate
CA: Cellosolve acetate

What is claimed is:

1. A compound of the formula:

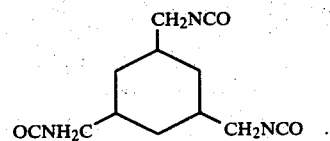

* * * * *